US008039666B2

(12) United States Patent
Cartolano et al.

(10) Patent No.: US 8,039,666 B2
(45) Date of Patent: Oct. 18, 2011

(54) SYNTHESIS OF AMINE BORANES

(75) Inventors: Anthony Rocco Cartolano, Orefield, PA (US); Sergei Vladimirovich Ivanov, Schnecksville, PA (US); Cheryl Irene Teich, Chalfont, PA (US); John Hiroshi Yamamoto, New Britain, PA (US)

(73) Assignees: Rohm and Haas Company, Philadelphia, PA (US); Air Products and Chemicals, Inc., Allentown, PA (US)

( * ) Notice: Subject to any disclaimer, the term of this patent is extended or adjusted under 35 U.S.C. 154(b) by 182 days.

(21) Appl. No.: 12/592,180

(22) Filed: Nov. 20, 2009

(65) Prior Publication Data
US 2010/0130780 A1    May 27, 2010

(51) Int. Cl.
*C07F 5/02* (2006.01)
(52) U.S. Cl. .......................................... 564/9
(58) Field of Classification Search ................ 564/9
See application file for complete search history.

(56) References Cited

U.S. PATENT DOCUMENTS

| 3,013,016 | A | 12/1961 | Haberland et al. |
| 3,192,217 | A | 6/1965 | Marshall |
| 5,144,032 | A | 9/1992 | Arduengo |
| 5,516,909 | A | 5/1996 | Sullivan |
| 5,565,615 | A | 10/1996 | Holzner et al. |
| 5,565,625 | A | 10/1996 | Howe et al. |
| 6,060,623 | A | 5/2000 | Iwasaki |
| 2004/0147781 | A1 | 7/2004 | Huang et al. |

FOREIGN PATENT DOCUMENTS
GB    909390 A    10/1962

*Primary Examiner* — Peter O Sullivan
(74) *Attorney, Agent, or Firm* — Kenneth Crimaldi

(57) ABSTRACT

A method for preparing an amine borane from an alkali metal borohydride and an amine salt. The alkali metal borohydride is allowed to react with 0.95 to 1.05 equivalents of the amine salt in a solvent which contains water and an amine.

6 Claims, No Drawings

SYNTHESIS OF AMINE BORANES

This application claims the benefit of priority under 35 U.S.C. §119(e) of U.S. Provisional Patent Application No. 61/200,218 filed on Nov. 25, 2008.

BACKGROUND

This invention relates generally to a method for preparing amine boranes from sodium borohydride and an amine salt.

Processes for production of amine boranes from sodium borohydride and amine salts are well known, and the reaction usually is carried out in an organic solvent in which sodium borohydride is soluble. For example, U.S. Pat. No. 6,060,623 describes preparation of amine boranes from sodium borohydride and amine salts in an organic solvent, e.g., 1,2-dimethoxyethane. In this process, the initial reaction mixture must be distilled to remove the solvent prior to isolation of the amine borane product.

The problem addressed by this invention is to provide a more efficient process for producing amine boranes from sodium borohydride and amine salts, without the use of additional solvents for the borohydride starting material.

STATEMENT OF INVENTION

The present invention is directed to a method for preparing amine boranes from an alkali metal borohydride and an amine salt. The method comprises allowing the alkali metal borohydride to react with 0.95 to 1.05 equivalents of the amine salt in a solvent comprising: (i) an amine which is a basic form of the amine salt; and (ii) water; wherein a weight ratio of total water in the solvent to alkali metal borohydride is from 0.5:1 to 2.7:1; and wherein the solvent contains no more than 5 wt % of solvents other than water and the amine.

DETAILED DESCRIPTION

Unless otherwise specified, all percentages herein are stated as weight percentages and temperatures are in ° C. Amounts in parts per million (ppm) are on the basis of weight/volume. In cases where the alkali metal borohydride is added as a dihydrate, ratios of amounts relative to an amount of alkali metal borohydride are relative to the contained alkali metal borohydride and not the dihydrate.

An "alkyl" group is a saturated hydrocarbyl group having from one to twenty carbon atoms, and may be linear, branched or cyclic. In some embodiments of the invention, alkyl groups are linear or branched, alternatively they are linear. In some embodiments, alkyl groups have from one to six carbon atoms, alternatively from one to four carbon atoms. A "hydrocarbon solvent" is any material essentially containing only carbon and hydrogen and which is a liquid at 0° C. at a pressure of 100 kPa. Hydrocarbon solvents may contain trace levels, i.e., less than 0.5%, of elements other than carbon and hydrogen as impurities. In some embodiments of the invention, hydrocarbon solvents are aliphatic hydrocarbons, alicyclic hydrocarbons, aromatic hydrocarbons or mixtures thereof; alternatively, saturated aliphatic hydrocarbons and/or aromatic hydrocarbons, alternatively $C_4$-$C_{16}$ saturated aliphatic hydrocarbons and/or $C_7$-$C_{20}$ aromatic hydrocarbons. Aromatic hydrocarbons are those containing an aromatic ring, which may have alkyl substituents. Especially preferred hydrocarbon solvents include mineral oil, toluene, xylenes, ethylbenzene, $C_6$-$C_{16}$ saturated aliphatic hydrocarbons, and mixtures thereof.

The reaction of an alkali metal borohydride with an amine is shown in general form in the following equation

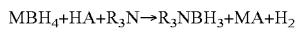

wherein M is an alkali metal cation; A is a conjugate base derived from a mineral acid, boric acid or carbonic acid and R may represent the same or different alkyl groups and/or hydrogen, provided that at least two alkyl groups are present. Preferably, the alkyl groups are $C_1$-$C_4$ alkyl groups, alternatively methyl or ethyl. Preferably, R does not represent hydrogen, and the amine is a trialkylamine. Preferably, M is sodium or potassium. Preferably the acid, HA is hydrochloric acid or sulfuric acid. In some embodiments, the amine hydrochloride is pre-formed, and the equation becomes

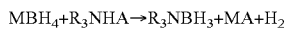

In these embodiments, preferably free amine and water are added as solvents.

The solvent, as the term is used herein, includes all water present, including any water of hydration from the alkali metal borohydride, and any water present in aqueous acid, in those embodiments where the amine salt is generated in situ from the amine and an acid. Preferably, the weight ratio of water in the solvent to the alkali metal borohydride is at least 0.7:1, alternatively at least 0.8:1, alternatively at least 0.9:1, alternatively at least 1:1, alternatively at least 1.5:1; preferably the ratio is no more than 2.5:1, alternatively no more than 2.2:1, alternatively no more than 2:1.

Preferably, the reaction occurs at a temperature in the range from 5° C. to 5° C. below the atmospheric-pressure boiling point of the solvent. In some embodiments, the temperature is at least 10° C., alternatively at least 15° C.; and preferably no greater than 100° C., alternatively no greater than 70° C., alternatively no greater than 50° C.

In some embodiments of the invention, the solvent contains no more than 5% of any solvent other than water and said amine. In these embodiments, preferably the weight ratio of total water in the solvent to alkali metal borohydride is from 0.5:1 to 2.7:1, alternatively from 0.8:1 to 2.7:1, alternatively from 1:1 to 2.7:1, alternatively from 1.5:1 to 2.7:1, alternatively from 1:1 to 2.5:1, alternatively from 1.5:1 to 2.5:1. In these embodiments, preferably the alkali metal borohydride is sodium borohydride which is introduced in the form of its dihydrate. In these embodiments, preferably, the weight ratio of free amine, i.e., amine not in the form of a salt, to alkali metal borohydride is from 1:1 to 6:1, alternatively from 1.5:1 to 6:1, alternatively from 2:1 to 6:1, alternatively from 2:1 to 5:1, alternatively from 2.5:1 to 4.5:1.

In some embodiments of the invention, the solvent further comprises a hydrocarbon solvent or a combination of hydrocarbon solvents. In these embodiments, preferably the weight ratio of total water to alkali metal borohydride is from 0.5:1 to 2.5:1, alternatively from 0.5:1 to 2:1, alternatively from 0.7:1 to 2:1, alternatively from 0.7:1 to 1.5:1. In these embodiments, preferably the weight ratio of hydrocarbon solvent(s) to alkali metal borohydride is from 1.5:1 to 12:1, alternatively from 2:1 to 12:1, alternatively from 2:1 to 10:1, alternatively from 1.5:1 to 8:1 In these embodiments, preferably the hydrocarbon solvent(s) is from 25 wt % to 70 wt % of the total weight of reactants and solvents, alternatively from 30 wt % to 65 wt %, alternatively from 30 wt % to 60 wt %, alternatively from 35 wt % to 60 wt %. In these embodiments, preferably the total amine, free amine plus the weight of amine contained in an amine salt, is at least 20 wt % of the total weight of reactants and solvents, alternatively at least 22 wt %, alternatively at least 24 wt %; and preferably no more than 40 wt %, alternatively no more than 36 wt %, alternatively from no more than 34 wt %. In these embodiments, preferably the total water, free water plus the weight of water contained in aqueous acid or hydrates, is at least 5 wt % of the total weight of reactants and solvents, alternatively at least 6 wt %, alternatively at least 7 wt %, alternatively at least 8 wt %; and preferably no more than 15 wt %, alternatively no more than 14 wt %, alternatively from no more than 13 wt %, alternatively no more than 12 wt %.

Preferably, the solvent contains no more than 5%, alternatively no more than 2% of solvents in which the alkali metal borohydride is soluble to an extent of at least 2%. Solvents in which alkali metal borohydrides are soluble include $C_3$-$C_8$ aliphatic amines, $C_3$-$C_8$ cyclic amines, $C_3$-$C_8$ diamines, $C_3$-$C_8$ alkanolamines, $C_5$-$C_{10}$ aromatic amines, $C_4$-$C_{12}$ methyl ethers of ethylene glycol and ethylene glycol oligomers, and $C_2$-$C_8$ amides. The aliphatic amines include mono-, di- and tri-alkyl amines, especially mono-alkyl amines, especially primary and secondary mono-alkyl amines. The aromatic amines include pyridine. The best amide solvents include N,N-dialkyl amides, especially aliphatic amides. Commonly used solvents include n-propylamine, isopropylamine, isobutylamine, sec-butylamine, n-butylamine, n-pentylamine, 1,2-dimethoxyethane, diethylene glycol dimethyl ether, pyridine, dimethylformamide, and dimethylacetamide.

EXAMPLES

Solid Sodium Borohydride with Solid Triethylamine Hydrochloride (NEt$_3$HCl) in Toluene at Room Temperature A three-neck flask containing a solids addition funnel, thermometer and a nitrogen gas purge was charged with 10 grams of SBH AF Grans (SBH with particle size larger than 80 mesh and smaller than 40 mesh). Then 100 mL of anhydrous toluene and 30 mL of NEt$_3$ were added. This slurry was stirred and 1 equivalent of solid NEt$_3$HCl (36.2 g) was added. No gas was evolved during the addition process. The reaction was stopped. No reaction; Yield=0%.

Sodium Borohydride in Isopropylamine and Solid NEt$_3$HCl

A three-neck flask containing a solids addition funnel, thermometer and a nitrogen gas purge was charged with 10 grams of SBH AF Grans, 90 grams of isopropylamine and 50 mL triethylamine. The resulting solution was stirred and 1 equivalent of solid NEt$_3$HCl (36.2 g) was added over a 3 hour period. Gas was instantaneously produced upon adding the solid NEt$_3$HCl. After the addition was completed, the slurry was stirred for an additional 3 hours at which time 50 mL of deionized water was added. The resulting two-phase solution was placed into a separatory funnel. Both the isopropylamine and water phases were analyzed by $^1$H and $^{11}$B NMR. The top isopropylamine layer contained 98% NH$_2^i$PrBH$_3$ and 2% NEt$_3$BH$_3$.

Spectroscopic data for NEt$_3$BH3: $^{11}$B NMR (tol d$^8$), δ-30.8 ppm, (q, $J_{B-H}$=98.3 Hz, 1B). $^1$H (tol d$^8$) δ=2.32 ppm (q, j$^{1-3}$=7.2 Hz, 6H) δ 0.84 ppm, (t, $J_{H-H}$=7.3 Hz, 9H)

Spectroscopic data for NH$_2^i$PrBH$_3$: $^{11}$B (tol d$^8$)=-38.7 ppm (q, $J_{B-H}$=94.5 Hz., 1B) $^1$H (tol d$^8$) ϵ=2.66 ppm, (sep, 1H, $J_{H-H}$=6.45 Hz); δ=2.27 ppm,(dd, $J_{H-H}$=4.5 Hz, 2H); δ 1.42 ppm, (s, 3H); δ 0.92 ppm, (d, 6H $J_{H-H}$=9.26 Hz)

Synthetic Sodium Borohydride Dihydrate with 100 mL Toluene and Solid NEt$_3$HCl

A three-neck flask containing a solids addition funnel, thermometer and a nitrogen gas purge was charged with 10 grams of SBH AF Grans, 10 grams of water and 0.1 grams of NaOH. The slurry was stirred for 24 hours until a solid mass formed. Then 100 mL of anhydrous toluene and 30 mL of NEt$_3$ were added. This slurry was stirred and 1 equivalent of solid NEt$_3$HCl (36.2 g) was added so that the temperature of the reaction did not increase above 40° C.

A large amount of gas evolved when the temperature of the reaction rose above 30° C. After 6 hours, 60 mL of water were added to dissolve all of the solids in the reaction pot. The resulting two-phase solution was placed into a separatory funnel and the bottom phase was washed with 3×100 mL of fresh toluene. All of the toluene phases were combined. Both the toluene and water phases were analyzed by $^1$H and $^{11}$B NMR.

Spectroscopic data for NEt$_3$BH$_3$. $^{11}$B NMR (tol d$^8$), δ-30.8 ppm, (q, $J_{B-H}$=98.3 Hz, 1B). $^1$H (tol d$^8$) δ=2.32 ppm (q, j$^{1-3}$=7.2 Hz, 6H) δ 0.84 ppm, (t, $J_{H-H}$=7.3 Hz, 9H)

| Material charged | Amount charged | Amount recovered | Total amount recovered |
|---|---|---|---|
| SBH AF Grans | 10.0 g | | |
| Water | 10.0 g | | |
| NEt$_3$ | 25 g | | |
| Toluene | 100 mL (86.5 g) | 123.76 g | |
| NEt$_3$HCl | 36.2 g | | |
| Water added | 60 mL (60 g) | | 87.88 g |
| Toluene wash 1 | 100 mL (86.5 g) | 56.5 g | |
| Toluene wash 2 | 100 mL (86.5 g) | 70.50 g | |
| Toluene wash 3 | 100 mL (86.5 g) | 100.27 g | 383.03 g |
| Yield | 98% | | |

Synthetic Sodium Borohydride Dihydrate with 50 mL of Toluene and Solid NEt$_3$HCl A three-neck flask containing a solids addition funnel, thermometer and a nitrogen gas purge was charged with 10 grams of SBH AF Grans and 10 grams of water with 0.1 grams of NaOH. The slurry was stirred for 24 hours until a solid mass formed. Then 50 mL of anhydrous toluene and 10 mL of NEt$_3$ were added. This slurry was stirred and 1 equivalent of solid NEt$_3$HCl (36.3 g) was added so that the temperature of the reaction did not increase above 40° C.

A large amount of gas evolved when the temperature of the reaction rose above 30° C. After 6 hours, 60 mL of water were added to dissolve all of the solids in the reaction pot. The resulting two-phase solution was placed into a separatory funnel and the bottom phase was washed with 3×30 mL of fresh toluene. All of the toluene phases were combined. Both the toluene and water phases were analyzed by $^1$H and $^{11}$B NMR.

Spectroscopic data for NEt$_3$BH$_3$. $^{11}$B NMR (tol d$^8$), δ-30.8 ppm, (q, $J_{B-H}$=98.3 Hz, 1B). $^1$H (tol d$^8$) δ=2.32 ppm (q, j$^{1-3}$=7.2 Hz, 6H) δ 0.84 ppm, (t, $J_{H-H}$=7.3 Hz, 9H)

| Material charged | Amount charged | Amount recovered | Total amount recovered |
|---|---|---|---|
| SBH AF Grans | 10.0 g | | |
| Water | 10.0 g | | |
| NEt$_3$ | 10 mL (7.26 g) | | |
| Toluene | 50 mL (43.5 g) | 73.25 g | |
| NEt$_3$HCl | 36.3 g | | |
| Water added | 60 mL (60.0 g) | | 82.43 g |
| Toluene wash 1 | 30 mL (25.95 g) | 26.89 g | |

| Material charged | Amount charged | Amount recovered | Total amount recovered |
|---|---|---|---|
| Toluene wash 2 | 30 mL (25.95 g) | 19.90 g | |
| Toluene wash 3 | 30 mL (35.95 g) | 25.74 g | 145.77 g |
| Yield | 98% | | |

Synthetic Sodium Borohydride Dihydrate with 50 mL Dodecane and Solid NEt$_3$HCl (to Little NEt$_3$HCl Added)

A three-neck flask containing a solids addition funnel, thermometer and a nitrogen gas purge was charged with 10 grams of SBH AF Grans and 10 grams of water with 0.1 grams of NaOH. The slurry was stirred for 24 hours until a solid mass formed. Then 50 mL of anhydrous dodecane and 10 mL of NEt$_3$ were added. This slurry was stirred and 1 equivalence of solid NEt$_3$HCl (26.4 g) was added so that the temperature of the reaction did not increase above 40° C.

A large amount of gas evolved when the temperature of the reaction rose above 30° C. After 6 hours, 60 mL of water were added to dissolve all of the solids in the reaction pot. The resulting two-phase solution was placed into a separatory funnel and the bottom phase was washed with 3×30 mL of fresh toluene. All of the toluene phases were combined. Both the dodecane and water phases were analyzed by $^1$H and $^{11}$B NMR.

Spectroscopic data for NEt$_3$BH$_3$. $^{11}$B NMR (tol d$^8$), δ-30.8 ppm, (q, J$_{B-H}$=98.3 Hz, 1B). $^1$H (tol d$^8$) δ=2.32 ppm (q, j$^{1-3}$=7.2 Hz, 6H) δ 0.84 ppm, (t, J$_{H-H}$=7.3 Hz, 9H)

| Material charged | Amount charged | Amount recovered | Total amount recovered |
|---|---|---|---|
| SBH AF Grans | 10.16 g | | |
| Water | 10.0 g | | |
| NEt$_3$ | 10 mL (7.26 g) | | |
| dodecane | 50 mL (37.5 g) | 65.15 g | |
| NEt$_3$HCl | 26.4 g | | |
| Water added | 60 mL | | 73.21 g |
| Dodecane wash 1 | 30 mL (22.5 g) | 21.20 g | |
| Dodecane wash 2 | 30 mL (22.5 g) | 23.37 g | |
| Dodecane wash 3 | 30 mL (22.5 g) | 27.80 g | 137.50 g |
| Yield | 44% | | |

KBH$_4$ and 50 mL Toluene and Solid NEt$_3$HCl

A three-neck flask containing a solids addition funnel, thermometer and a nitrogen gas purge was charged with 14.21 grams of KBH$_4$ 100 and 10 grams of water with 0.1 grams of NaOH. Then 50 grams of anhydrous toluene and 10 mL of NEt$_3$ were added. This slurry was stirred and 1 equivalent of solid NEt$_3$HCl (36.2 g) was added so that the temperature of the reaction did not increase above 40° C.

A large amount of gas evolved when the temperature of the reaction rose above 30° C. After 6 hours, 60 mL of water were added to dissolve all of the solids in the reaction pot. The resulting two-phase solution was placed into a separatory funnel and the bottom phase was washed with 3×30 mL of fresh toluene. All of the toluene phases were combined. Both the toluene and water phases were analyzed by $^1$H and $^{11}$B NMR.

Spectroscopic data for NEt$_3$BH$_3$. $^{11}$B NMR (tol d$^8$), δ-30.8 ppm, (q, J$_{B-H}$=98.3 Hz, 1B). $^1$H (tol d$^8$) δ=2.32 ppm (q, j$^{1-3}$=7.2 Hz, 6H) δ 0.84 ppm, (t, J$_{H-H}$=7.3 Hz, 9H)

| Material charged | Amount charged | Amount recovered | Total amount recovered |
|---|---|---|---|
| KBH$_4$ 100 | 14.21 g | | |
| Water | 10 g | | |
| NEt$_3$ | 10 mL (7.26 g) | | |
| Toluene | 50 mL (43.5 g) | 69.52 g | |
| NEt$_3$HCl | 36.2 g | | |
| Water added | 60 mL (60 g) | | 88.85 g |
| Toluene wash 1 | 30 mL (25.95 g) | 20.96 g | |
| Toluene wash 2 | 30 mL (25.95 g) | 21.82 g | |
| Toluene wash 3 | 30 mL (25.95 g) | 27.34 g | 139.64 g |
| Yield | 93% | | |

Synthetic Sodium Borohydride Dihydrate with 25 mL Toluene and Solid NEt$_3$HCl A three-neck flask containing a solids addition funnel, thermometer and a nitrogen gas purge was charged with 10 grams of SBH AF Grans and 10 grams of water with 0.1 grams of NaOH. The slurry was stirred for 24 hours until a solid mass formed. Then 25 mL of anhydrous toluene and 5 mL of NEt$_3$ were added. This slurry was stirred and 1 equivalent of solid NEt$_3$HCl (36.2 g) was added so that the temperature of the reaction did not increase above 40° C.

A large amount of gas evolved when the temperature of the reaction rose above 30° C. After 6 hours, 60 mL of water were added to dissolve all of the solids in the reaction pot. The resulting two-phase solution was placed into a separatory funnel and the bottom phase was washed with 3×30 mL of fresh toluene. All of the toluene phases were combined. Both the toluene and water phases were analyzed by $^1$H and $^{11}$B NMR.

Spectroscopic data for NEt$_3$BH$_3$. $^{11}$B NMR (tol d$^8$), δ-30.8 ppm, (q, J$_{B-H}$=98.3 Hz, 1B). $^1$H (tol d$^8$) δ=2.32 ppm (q, j$^{1-3}$=7.2 Hz, 6H) δ 0.84 ppm, (t, J$_{H-H}$=7.3 Hz, 9H)

| Material charged | Amount charged | Amount recovered | Total amount recovered |
|---|---|---|---|
| SBH AF Grans | 10.16 g | | |
| Water | 10.0 g | | |
| NEt$_3$ | 5 mL (3.63 g) | | |
| Toluene | 25 mL (21.62 g) | 49.29 g | |
| NEt$_3$HCl | 36.2 g | | |
| Water added | 60 mL | 72.44 g | 72.44 g |
| Toluene wash 1 | 15 mL (12.97 g) | 16.15 g | |
| Toluene wash 2 | 15 mL (12.97 g) | 16.16 g | |
| Toluene wash 3 | 15 mL (12.97 g) | 16.23 g | 97.81 g |
| Yield | 98% | | |

Synthetic Sodium Borohydride Dihydrate with 25 mL Xylenes and Solid NEt$_3$HCl A three-neck flask containing a solids addition funnel, thermometer and a nitrogen gas purge was charged with 10 grams of SBH AF Grans and 10 grams of water with 0.1 grams of NaOH. The slurry was stirred for 24 hours until a solid mass formed. Then 25 mL of anhydrous xylenes and 5 mL of NEt$_3$ were added. This slurry was stirred and 1 equivalent of solid NEt$_3$HCl (36.2 g) was added so that the temperature of the reaction did not increase above 40° C.

A large amount of gas evolved when the temperature of the reaction rose above 30° C. After 6 hours, 60 mL of water were added to dissolve all of the solids in the reaction pot. The resulting two-phase solution was placed into a separator funnel and the bottom phase was washed with 3×30mL of fresh xylenes. All of the xylenes phases were combined. Both the xylenes and water phases were analyzed by $^1$H and $^{11}$B NMR.

Spectroscopic data for NEt$_3$BH$_3$. $^{11}$B NMR (tol d$^8$), δ-30.8 ppm, (q, J$_{B-H}$=98.3 Hz, 1B). $^1$H (tol d$^8$) δ=2.32 ppm (q, j$^{1-3}$=7.2 Hz, 6H) δ 0.84 ppm, (t, J$_{H-H}$=7.3 Hz, 9H)

| Material charged | Amount charged | Amount recovered | Total amount recovered |
|---|---|---|---|
| SBH AF Grans | 10.10 g | | |
| Water | 10.0 g | | |
| NEt$_3$ | 5 mL (3.63 g) | | |
| Xylenes | 25 mL (21.5 g) | 48.56 g | |
| NEt$_3$HCl | 36.2 g | | |
| Water added | 60 mL | 61.19 g | 61.19 g |
| Xylenes wash 1 | 15 mL (12.9 g) | 17.70 g | |
| Xylenes wash 2 | 15 mL (12.9 g) | 7.29 g | |
| Xylenes wash 3 | 15 mL (12.9 g) | 5.17 g | 78.75 g |
| Yield | 98% | | |

Synthetic Sodium Borohydride Dihydrate with 25 mL Triethylamine and Solid NEt$_3$HCl A three-neck flask containing a solids addition funnel, thermometer and a nitrogen gas purge was charged with 10 grams of SBH AF Grans and 10 grams of water with 0.1 grams of NaOH. The slurry was stirred for 24 hours until a solid mass formed. Then 25 mL of anhydrous triethylamine was added. This slurry was stirred and 1 equivalent of solid NEt$_3$HCl (36.2 g) was added so that the temperature of the reaction did not increase above 40° C.

A large amount of gas evolved when the temperature of the reaction rose above 30° C. After 6 hours, 60 mL of water were added to dissolve all of the solids in the reaction pot. The resulting two-phase solution was placed into a separatory funnel and the bottom phase was washed with 3×5 mL of fresh NEt$_3$. All of the triethyl amine phases were combined. Both the triethylamine and water phases were analyzed by $^1$H and $^{11}$B NMR.

Spectroscopic data for NEt$_3$BH$_3$. $^{11}$B NMR (tol d$^8$), δ-30.8 ppm, (q, J$_{J-H}$=98.3 Hz, 1B). $^1$H (tol d$^8$) δ=2.32 ppm (q, j$^{1-3}$=7.2 Hz, 6H) δ 0.84 ppm, (t, J$_{H-H}$=7.3 Hz, 9H)

| Material charged | Amount charged | Amount recovered | Total amount recovered |
|---|---|---|---|
| SBH AF Grans | 10.10 g | | |
| Water | 10.0 g | | |
| NEt$_3$ | 25 mL (18.15 g) | 33.52 g | |
| NEt$_3$HCl | 36.2 g | | |
| Water added | 60 mL | 55.0 g | 55.0 g |
| NEt$_3$ wash 1 | 5 mL (3.63 g) | 0.55 g | |
| NEt$_3$ wash 2 | 5 mL (3.63 g) | 2.92 g | |
| NEt$_3$ wash 3 | 5 mL (3.63 g) | 3.19 g | 40.18 g |
| Yield | 96% | | |

Synthetic Sodium Borohydride Dihydrate with 100 mL Toluene and Preformed NEt$_3$HCl A three-neck flask containing a solids addition funnel, thermometer and a nitrogen gas purge was charged with 10 grams of SBH AF Grans, 10 grams of water and 0.1 grams of NaOH. The slurry was stirred for 24 hours until a solid mass formed. Another three-neck flask was charged with 1 eq of NEt$_3$ and 1 eq of 37% HCl. Then 100 mL of anhydrous toluene and 30 mL of NEt$_3$ were added. This slurry was stirred and the content of flask number one was added so that the temperature of the reaction did not increase above 40° C.

A large amount of gas evolved when the temperature of the reaction rose above 30° C. After 6 hours, 60 mL of water were added to dissolve all of the solids in the reaction pot. The resulting two-phase solution was placed into a separatory funnel and the bottom phase was washed with 3×100 mL of fresh toluene. All of the toluene phases were combined. Both the toluene and water phases were analyzed by $^1$H and $^{11}$B NMR.

Spectroscopic data for NEt$_3$BH$_3$. $^{11}$B NMR (tol d$^8$), δ-30.8 ppm, (q, J$_{B-H}$=98.3 Hz, 1B). $^1$H (tol d$^8$) δ=2.32 ppm (q, j$^{1-3}$=7.2 Hz, 6H) δ 0.84 ppm, (t, J$_{H-H}$=7.3 Hz, 9H)

| Material charged | Amount charged | Amount recovered | Total amount recovered |
|---|---|---|---|
| SBH AF Grans | 10.30 g | | |
| Water | 10.0 g | | |
| NEt$_3$ | 86.5 mL (62.80 g) | | |
| Toluene | 50 mL (43.25 g) | 105.97 g | |
| 39% HCl | 21.74 mL | | |
| Water added | 60 mL (60 g) | | 105.74 g |
| Toluene wash 1 | 100 mL (86.5 g) | 86.17 g | |
| Toluene wash 2 | 100 mL (86.5 g) | 77.86 g | |
| Toluene wash 3 | 100 mL (86.5 g) | 78.64 g | 348.64 g |
| Yield | 54% | | |

The following table summarizes the experiments above and the results.

TABLE 1

Synthesis of NEt$_3$BH$_3$ (1)

| Solvent | excess NEt$_3$ added, g | cont. mL | form of SBH, g | Form of NEt$_3$•HCl | NEt$_3$•HCl | wash, mL | react. temp. ° C. | % Yield NEt$_3$BH$_3$ By NMR |
|---|---|---|---|---|---|---|---|---|
| isopropyl amine | 90 | 50 | 10 | Pure | 1 eq | solid | 0 | 22 | 2 |
| toluene | 100 | 50 | 10 | Pure | 1 eq | solid | 0 | 22 | 0 |
| toluene | 100 | 25 | 10 | •2H$_2$O | 1 eq | solid | 3 × 100 | 22-40 | 98 |
| toluene | 50 | 10 | 10 | •2H$_2$O | 1 eq | solid | 3 × 30 | 22-40 | 98 |
| dodecane | 50 | 25 | 10 | •2H$_2$O | 0.72 eq | solid | 3 × 30 | 22-40 | 54 |

TABLE 1-continued

Synthesis of NEt₃BH₃ (1)

| Solvent | excess NEt₃ added, g | cont. mL | SBH, g | form of SBH | NEt₃•HCl | Form of NEt₃•HCl | wash, mL | react. temp. ° C. | % Yield NEt₃BH₃ By NMR |
|---|---|---|---|---|---|---|---|---|---|
| toluene | 50 | 25 | 14.21 | KBH₄ | 1 eq | solid | 3 × 30 | 22-40 | 93 |
| toluene | 25 | 5 | 10 | •2H₂O | 1 eq | solid | 3 × 15 | 22-40 | 98 |
| xylenes | 25 | 5 | 10 | •2H₂O | 1 eq | solid | 3 × 15 | 22-40 | 98 |
| NEt₃ | 25 | 0 | 10 | •2H₂O | 1 eq | solid | 3 × 5 | 22-40 | 96 |
| NEt₃ SBH to NEt₃HCl | 50 | 21.71 | 10 | •2H₂O | 1 eq | pre-formed | 3 × 100 | 22-40 | 54 |

The results of additional experiments are summarized in the following table.

| Borohydride | MBH₄, g | Mode of addition | Acid | conc. of acid | Reaction temperature | yield |
|---|---|---|---|---|---|---|
| NaBH₄*2H₂O | 10 | acid added | HCl | 37 wt % | RT to 40° C. | 97 |
| NaBH₄*2H₂O | 10 | performed | HCl | 37 wt % | RT to 40° C. | 98 |
| NaBH₄*2H₂O | 10 | acid added | H₂SO₄ | 98 wt % | RT to 40° C. | 0 |
| NaBH₄*2H₂O | 100 | acid added | HCl | 37 wt | RT to 40° C. | 80 |
| NaBH₄*2H₂O | 50 | acid added | HCl | 37 wt | RT to 40° C. | 74 |
| NaBH₄*2H₂O | 50 | preformed | HCl | 37 wt | RT to 40° C. | 85 |
| NaBH₄*2H₂O | 50 | preformed | HCl | 37 wt | 8° C. to 20° C. | 64 |
| KBH₄ | 12.25 | acid addition | HCl | 9.25 wt % | RT to 40° C. | 55 |
| KBH₄ | 12.25 | acid addition | HCl | 17.5 wt % | RT to 40° C. | 85 |
| KBH₄ | 12.25 | acid addition | HCl | 37 wt % | RT to 40° C. (18 h) | 65 |
| KBH₄ | 12.25 | acid addition | HCl | 37 wt % | RT to 40° C. (6 h) | 61 |
| KBH₄ | 12.25 | acid addition | H₂SO₄ | 75 wt % | RT to 40° C. | 79 |
| KBH₄ | 12.25 | acid addition | H₂SO₄ | 50 wt % | RT to 40° C. | 51 |
| KBH₄ | 12.25 g | acid addition | H₂SO₄ | 25 wt % | RT to 40° C. | 44 |
| Plant-made NaBH₄*2H₂O | 20 | acid addition | HCl | 37 wt % | RT to 35° C. | 68 |
| Plant-made NaBH₄*2H₂O | 20 | preformed | HCl | 37 wt % | RT to 35° C. | 62 |
| Synthetic NaBH₄*2H₂O | 20 | preformed | HCl | 37 wt % | RT to 35° C. | 71 |

RT = room temperature, i.e., 20-25° C.

The invention claimed is:

1. A method for preparing an amine borane from an alkali metal borohydride and an amine salt; said method comprising allowing the alkali metal borohydride to react with 0.95 to 1.05 equivalents of the amine salt in a solvent comprising: (i) a free amine which is a basic form of said amine salt; and (ii) water; wherein a weight ratio of total water to alkali metal borohydride is from 0.5:1 to 2.7:1; and wherein the solvent contains no more than 5 wt % of solvents other than water and said amine.

2. The method of claim 1 in which the weight ratio of total water in the solvent to alkali metal borohydride is from 1:1 to 2.7:1.

3. The method of claim 2 in which the amine salt is a trialkylamine salt.

4. The method of claim 3 in which a weight ratio of free amine to alkali metal borohydride is from 1:1 to 6:1.

5. The method of claim 4 in which the alkali metal borohydride is sodium borohydride, which is added in the form of a dihydrate.

6. The method of claim 4 in which the alkali metal borohydride is potassium borohydride.

* * * * *